(12) United States Patent
Abdel-Aziz

(10) Patent No.: US 6,513,527 B1
(45) Date of Patent: Feb. 4, 2003

(54) BIBRONCHIAL DOUBLE LUMEN TUBE

(75) Inventor: Ahmed Abdel-Aziz, Jacksonville, MS (US)

(73) Assignee: University of Mississippi Medical Center, Jackson, MS (US)

( * ) Notice: Subject to any disclaimer, the term of this patent is extended or adjusted under 35 U.S.C. 154(b) by 256 days.

(21) Appl. No.: 09/593,970

(22) Filed: Jun. 13, 2000

(51) Int. Cl.[7] .............................................. A61M 16/00
(52) U.S. Cl. ........................... 128/207.14; 128/200.26; 128/207.15; 604/164.01; 604/523
(58) Field of Search ....................... 128/200.24, 200.26, 128/201.24, 202.27, 207.14, 207.15, 207.18, 911, 912; 604/39, 43, 108, 101.01, 170.02, 101.04, 164.01, 101.05, 164.12, 164.05, 171, 164.08, 523, 170.528, 533–535, 537, 284, 94.01, 95.04, 103, 103.03, 165.01; 600/432–435

(56) References Cited

U.S. PATENT DOCUMENTS

| | | | | |
|---|---|---|---|---|
| 4,840,172 A | * | 6/1989 | Augustine et al. ..... | 128/207.14 |
| 5,065,755 A | * | 11/1991 | Klafta ................... | 128/200.26 |
| 5,263,478 A | * | 11/1993 | Davis .................... | 128/200.26 |
| 5,309,906 A | * | 5/1994 | LaBombard ........... | 128/207.14 |
| 5,499,625 A | * | 3/1996 | Frass et al. ............ | 128/200.26 |
| 5,588,424 A | * | 12/1996 | Insler et al. ........... | 128/200.24 |
| 5,660,175 A | * | 8/1997 | Dayal .................... | 128/200.26 |
| 5,904,648 A | * | 5/1999 | Arndt et al. ................ | 600/110 |
| 5,957,134 A | * | 9/1999 | Lee ........................ | 128/207.14 |
| 6,443,156 B1 | * | 9/2002 | Niklason et al. ........ | 128/207.14 |

FOREIGN PATENT DOCUMENTS

GB  2168256  * 6/1986

* cited by examiner

Primary Examiner—Glenn K. Dawson
Assistant Examiner—Mital Patel
(74) Attorney, Agent, or Firm—Needle & Rosenberg, P.C.

(57) ABSTRACT

An embodiment of the present invention described and shown in the specification and drawings is a double lumen breathing tube for ventilating at least one lung of a subject. The distal ends of the tubes are predisposed to be spaced-apart and when in position in the airway of a human subject, each tube fits into a mainstem bronchus. A structure for temporarily positioning the distal ends of the tubes into a contacting or closely adjacent position is provided to facilitate introducing the breathing tube into the airway and for removing the breathing tube from the airway. Moreover, a method of ventilating at least one lung of a human subject is provided. This abstract is provided to comply with the rules requiring an abstract which will allow a searcher or other reader to ascertain quickly the subject matter of the technical disclosure. It is submitted with the understanding that it will not be used to interpret or limit the scope or meaning of the claims. 37 C.F.R. §1.72(b).

18 Claims, 11 Drawing Sheets

FIG. 4D1

BIBRONCHIAL DOUBLE LUMEN TUBE

BACKGROUND OF THE INVENTION

1. Field of the Invention

The present invention relates generally to endobronchial tubes for insertion through the mouth or nasal passages of a patient to facilitate artificial ventilation of the respiratory system. More particularly, this invention relates to endobronchial tubes with a double lumen and balloon cuffs for selective ventilation of one or both lungs of a patient.

2. Background Art

It is a common practice to provide human medical patients with artificial ventilation during surgery or in emergency situations. For example, accident victims will frequently require CPR or intubation by a paramedic in an emergency vehicle or by an anesthesiologist in an operating room. In such situations, intubation is accomplished by insertion of a breathing tube through the patient's mouth or nasal passages into the airway passage. Such devices have generally comprised a relatively pliable tube that is connectable to a respirator or other air supply mechanism for introduction of air into the lungs. An improvement to breathing tubes includes an inflatable-deflatable bag-like structure or balloon "cuff" around the exterior of the tube. The balloon cuff is conventionally located in a position along the breathing tube to engage the inner wall of the pharynx, larynx, or trachea, depending upon the specific breathing tube design. When the tube is in place, the cuff is inflated and forms an air tight seal between the tube and the surrounding body tissue to prevent the escape of air pumped from the respirator into the lungs.

Both single lumen and double lumen breathing tubes are known. Typically, a single lumen breathing tube is an elongated tube that extends into the trachea of a patient and includes one inflatable balloon cuff near its distal end. Commonly, the double lumen breathing tube is referred to as an endobronchial tube and, in addition to one lumen which extends to the trachea, has a second longer lumen which extends into the bronchus of a patient upon intubation. Typically, the double lumen breathing tube or endobronchial tube includes two inflatable balloon cuffs. The double lumen breathing tubes, such as the well known "Carlens" and "Robertshaw" tubes, allow for independent control of each lung through the separate lumens. One bronchus may be blocked by occluding one of the lumens at a position external to the patient, in order to isolate a particular lung.

The balloon cuffs are thin walled, high volume, and low pressure chambers or vessels that are designed to avoid compromising the blood flow in the tracheal or bronchial wall when inflated. Balloon cuffs are made of a soft expandable plastic and can be inflated by detachable syringes that are connected to smaller lumens or channels at the proximal end of the breathing tube. The seals formed by the inflated cuffs preclude the air that has been forced into the patient's lungs from escaping through the trachea or bronchus. Additionally, the seals formed by the inflated cuffs provide a barrier to the flow of blood and secretions.

The double lumen breathing tubes offer an anesthesiologist the ability to ventilate selectively either the right or left lung or both lungs as required. One potential problem with currently used double lumen breathing tubes, however, is the obstruction of the right upper lobe bronchus. Correct placement of the currently available double lumen tubes requires confirmation with fiberoptic bronchoscopy. Moreover, currently available double lumen tubes can be easily displaced after correct placement, especially when the patient is repositioned on the operating table.

The present invention provides an improvement over the prior art because its proper positioning is assured by its unique design; thus, the need for fiberoptic bronchoscopy is minimized. Moreover, the present invention is more securely placed with less risk for malposition after placement, compared to currently available double lumen tubes.

SUMMARY OF THE INVENTION

The present invention comprises a double lumen breathing tube comprising two tubes disposed adjacent to each other. Each tube has a lumen, a proximal end, a distal end and a length extending between the proximal and distal ends. The two tubes are fixedly attached to each other along a portion of their respective lengths. A first branch section is a section of length of the first tube extending from the distal end of the first tube to a proximal location at which the first and second tubes are fixedly attached to each other. A second branch section is a section of length of the second tube extending from the distal end of the second tube to a proximal location at which the first and second tubes are fixedly attached to each other. The first branch section is preferably longer than the second branch section. The first branch section and the second branch section are also preferably predisposed to be spaced-apart from each other. Each proximal end can be individually attached to a ventilating machine, or respirator, so that either one or both tubes can be connected to a ventilation source at any given time.

As one skilled in the art will appreciate, the predisposition of the first branch section and the second branch section to be spaced-apart from each other hinders the insertion of the double lumen tube into the patient's airway. Accordingly, the present invention also provides a means for temporarily positioning the first branch section and the second branch section in contact with each other along at least a portion of their respective lengths. In one embodiment, the temporarily positioning means is a stylet having a central body portion connecting two spaced-apart arms that are disposed substantially parallel to each other so that the stylet is substantially U-shaped in plan view. When each arm of the stylet is positioned within a respective lumen of the double lumen tube, at least a portion of the first and second branch sections are in contact.

In another embodiment of the present invention, the temporarily positioning means comprises a sleeve. The sleeve has an interior surface of a size to complementarily receive the first and second tubes therein. When the sleeve is moved toward the distal ends of the first and second tubes so that the distal end of at least the second tube is disposed within the sleeve, at least a portion of the first and second branch sections contact each other. When the clinician moves the sleeve proximally after insertion into the patient's airway so that the distal end of the sleeve is proximal or adjacent to the point where the two tubes are fixedly attached, the first branch section and the second branch section move apart to their predisposed spaced-apart position.

The present invention further provides another temporarily positioning means comprising a primary spring and one or more wires interconnecting the primary spring and the distal ends of the two tubes. The wires extend along and are disposed adjacent to the first branch section and the second branch section respectively. The bottom ends of the wires are secured to the distal end of the tubes, and the wire also extends along the joined portion of the length of the first and second tubes that are fixedly attached to each other. The primary spring is movable between an extended position and a compressed position. When the primary spring is in the extended position, a portion of the first and second branch sections are in contact with each other. Alternatively, when the primary spring is compressed, the first branch section and the second branch section are spread apart from each other to their predisposed spaced-apart position.

Regardless of the temporarily positioning means used, once the double lumen breathing tube has passed through the vocal cords, the temporarily positioning means is discontinued or released, allowing the first branch section and the second branch section to move to their predisposed spaced-apart positions. Therefore, the first branch section is aligned to be positioned in the left mainstem bronchus and the second branch section is aligned to be positioned in the right mainstem bronchus.

Also, the present invention allows the clinician to place the double lumen breathing tube so that the first branch section is positioned in the left mainstem bronchus, and the second branch section is positioned in the right mainstem bronchus without obstructing the opening into either mainstem bronchus.

BRIEF DESCRIPTION OF THE FIGURES OF THE DRAWINGS

FIG. 4D1 is a side view of the plate and protrusion shown in FIG. 4D.

DETAILED DESCRIPTION OF THE INVENTION

The present invention is more particularly described in the following examples that are intended as illustrative only since numerous modifications and variations therein will be apparent to those skilled in the art. As used in the specification and in the claims, "a", "an", or "the" can mean one or more, depending upon the context in which it is used. The present invention is now described with reference to the figures, in which like numbers indicate like parts throughout the figures.

Figure 1:
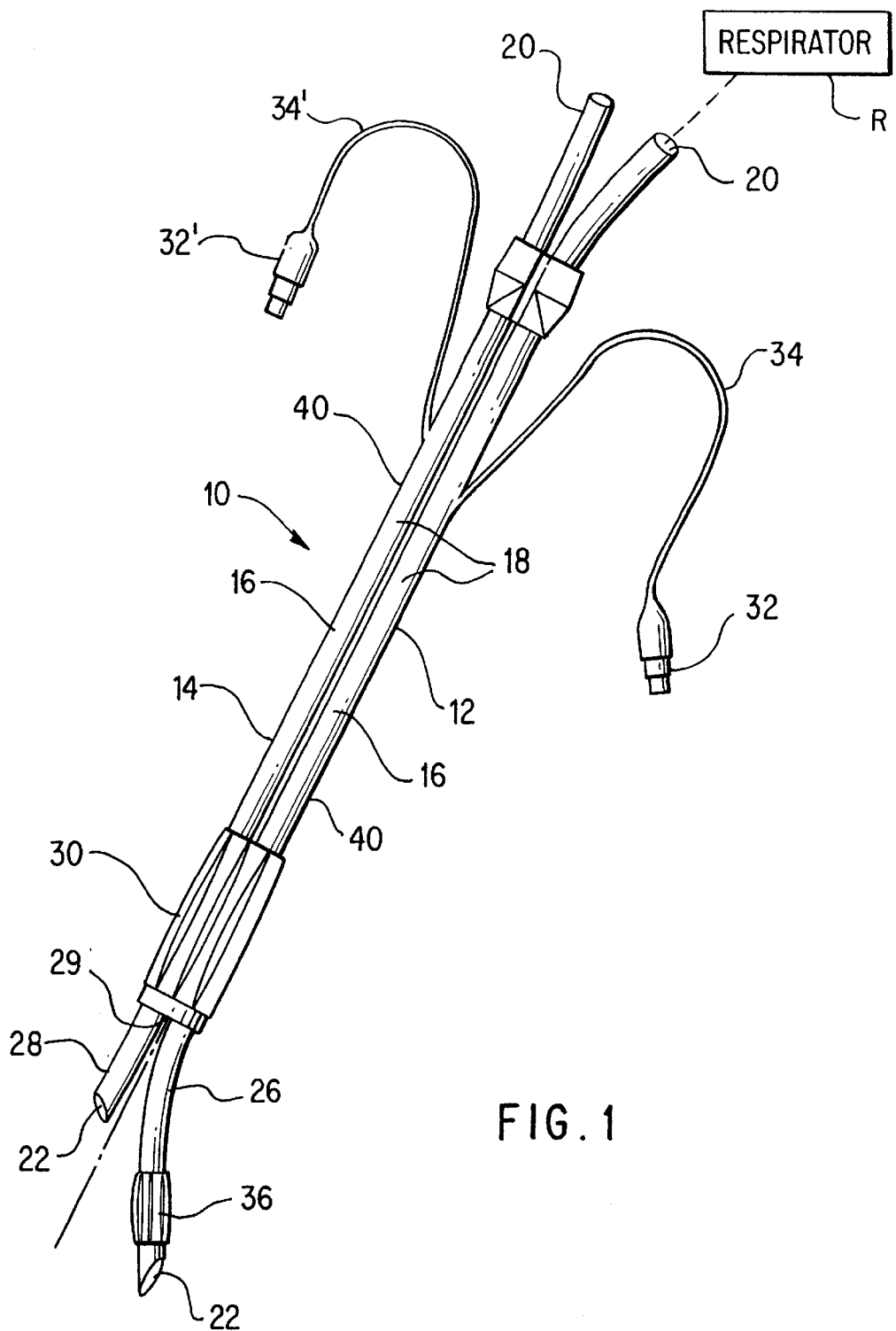
FIG. 1 is a side elevational view of the double lumen tube of the present invention.

Referring first to FIG. 1, the present invention comprises a double lumen breathing tube 10 comprising two tubes 12, 14, including a first tube 12 and a second tube 14, that are disposed adjacent to each other. Each tube has a lumen 16, an exterior surface 18, a proximal end 20, a distal end 22 and a length extending between the proximal and distal ends 20, 22. The two tubes 12, 14 are attached to each other along a portion of their respective lengths. A first branch section 26 is a section of length of the first tube 12 extending from the distal end 22 of the first tube 12 to a location at which the first tube 12 and the second tube 14 are fixedly attached to each other. A second branch section 28 is a section of length of the second tube 14 extending from the distal end 22 of the second tube 14 to the same location at which the first tube 12 and the second tube 14 are fixedly attached to each other. The most distal, or lowermost, location 29 at which the first and second tubes 12, 14 are connected to each other is the point below which the first and second branch sections 26, 28 begin, i.e., the proximal ends of the first and second branch sections 26, 28.

The first branch section 26 is preferably longer than the second branch section 28. Also, the first branch section 26 and second branch section 28 are preferably predisposed to be spaced-apart from each other. Each proximal end 20 of the first and second tubes 12, 14 can be individually attached to a ventilating machine or respirator R (as shown schematically in FIG. 1) so that either one or both tubes 12, 14 can be connected to a ventilation source at any given time. The preferred materials used to form the tubes 12, 14 include polyvinyl chloride (PVC) and silicon, but one skilled in the art will appreciate that other surgical-grade materials can be used, such as plastics and polymers.

As noted above, two tubes 12, 14 are fixedly attached together along a portion of their lengths. By "fixedly attached," it is contemplated that the first and second tubes 12, 14 do not become separated or spaced-apart from each other along the portion that is "fixedly attached" during the surgical procedure. In the embodiment using tubes 12, 14 formed of PVC, the preferred way to fixedly attach sections of the tubes 12, 14 together is by forming or molding the two tubes 12, 14 to be integrally formed together. Other designs connect the two tubes 12, 14, such as by a chemical adhesive or by physical structures to stationarily position a portion of the two tubes 12, 14 relative to each other (for example, using a main inflation cuff 30 which is discussed below).

The preferred length of the first branch section 26 is 5 centimeters. A more preferred length is 3 centimeters, and the most preferred length of the first branch section 26 is 4 centimeters. The preferred length of the second branch section 28 is 2.5 centimeters. A more preferred length is 1.5 centimeters, and the most preferred length of the second branch section 28 is 2 centimeters. Thus, the first branch section 26 of the first tube 12 is preferably 1.5 centimeters to 3.5 centimeters longer than the second branch section 28 of the second tube 14.

Further, the present invention provides that the first branch section 26 of the first tube 12 and the second branch section 28 of the second tube 14 are predisposed to be spaced-apart from each other when in position in the airway of a patient. In one embodiment, when the second tube 14 is oriented substantially linearly along its length, the first branch section 26 is predisposed to form an angle of approximately 35 degrees to 50 degrees relative to the substantially linearly oriented second tube 14. The preferred angle is 40 degrees. A more preferred angle is 50 degrees, and the most preferred angle is 45 degrees. This angle matches the angle that the left mainstem bronchus makes relative to the trachea when the left mainstem bronchus branches off the trachea. Thus, the first tube 12 of the present invention is designed to fit easily within the left mainstem bronchus to ventilate the left lung.

Alternatively, when the first tube 12 is oriented substantially linearly along its length, the second branch section 28 of the second tube 14 is predisposed to form an angle of approximately 15 degrees to 35 degrees to the substantially linearly oriented first tube 12. The preferred angle is 20 degrees. A more preferred angle is 30 degrees, and the most preferred angle is 25 degrees. This angle matches the angle that the right mainstem bronchus makes relative to the trachea when the right mainstem bronchus branches off the trachea. Thus, the second tube 14 of the present invention is designed to fit easily within the right mainstem bronchus to ventilate the right lung.

In another design, both the first and second branch sections 26, 28 form an angle relative to the longitudinal axis of the tube 10 so that neither branch section 26, 28 is linear. In this design, the preferred angle between the two branch sections 26, 28 is 60 degrees. A more preferred angle is 80 degrees, and the most preferred angle is 70 degrees.

In designing and manufacturing the present invention, the double lumen tube 10 is formed by molding the two tubes 12, 14 in the desired position, which causes the first and second branch sections 26, 28 to be predisposed to be spaced-apart from each other. That is, when the two tubes 12, 14 are molded together in the desired positions relative to each other, the material will return to its originally molded position after being repositioned.

Figure 2A:
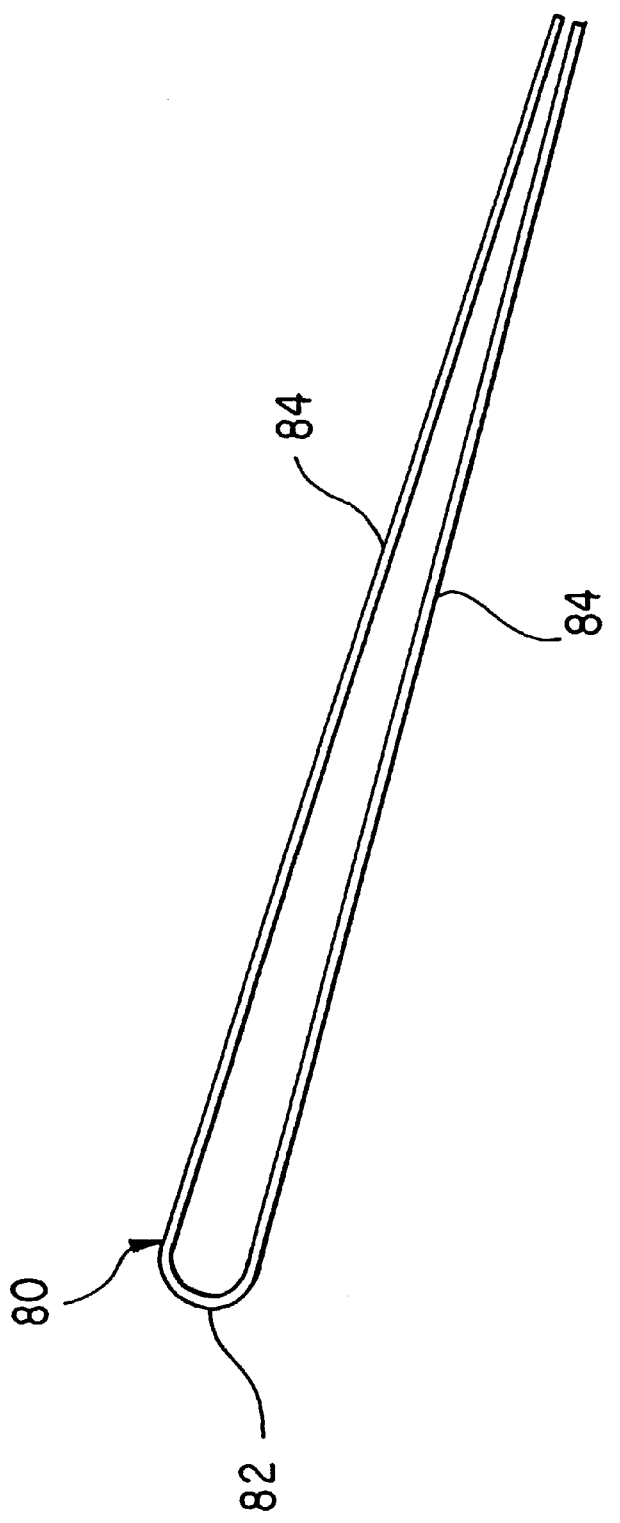
FIG. 2A is a top plan view of a stylet of the present invention.

Because it would be difficult to introduce into the airway of the patient the breathing tube 10 with the first branch section 26 and the second branch section 28 in their predisposed spaced-apart position, the present invention includes either a structure or a means for temporarily positioning the first branch section 26 and the second branch section 28 in contact with (which is defined to include being closely adjacent to each other) at least along a portion of their respective lengths. In one embodiment shown in FIGS. 2A–2C, the temporarily positioning means is a stylet 80. The stylet 80 has a central body 82 portion connecting two spaced-apart arms 84 that are disposed substantially parallel or at a near parallel orientation to each other so that the stylet is substantially U-shaped in plan view, as shown in FIG. 2A.

Figure 2B:
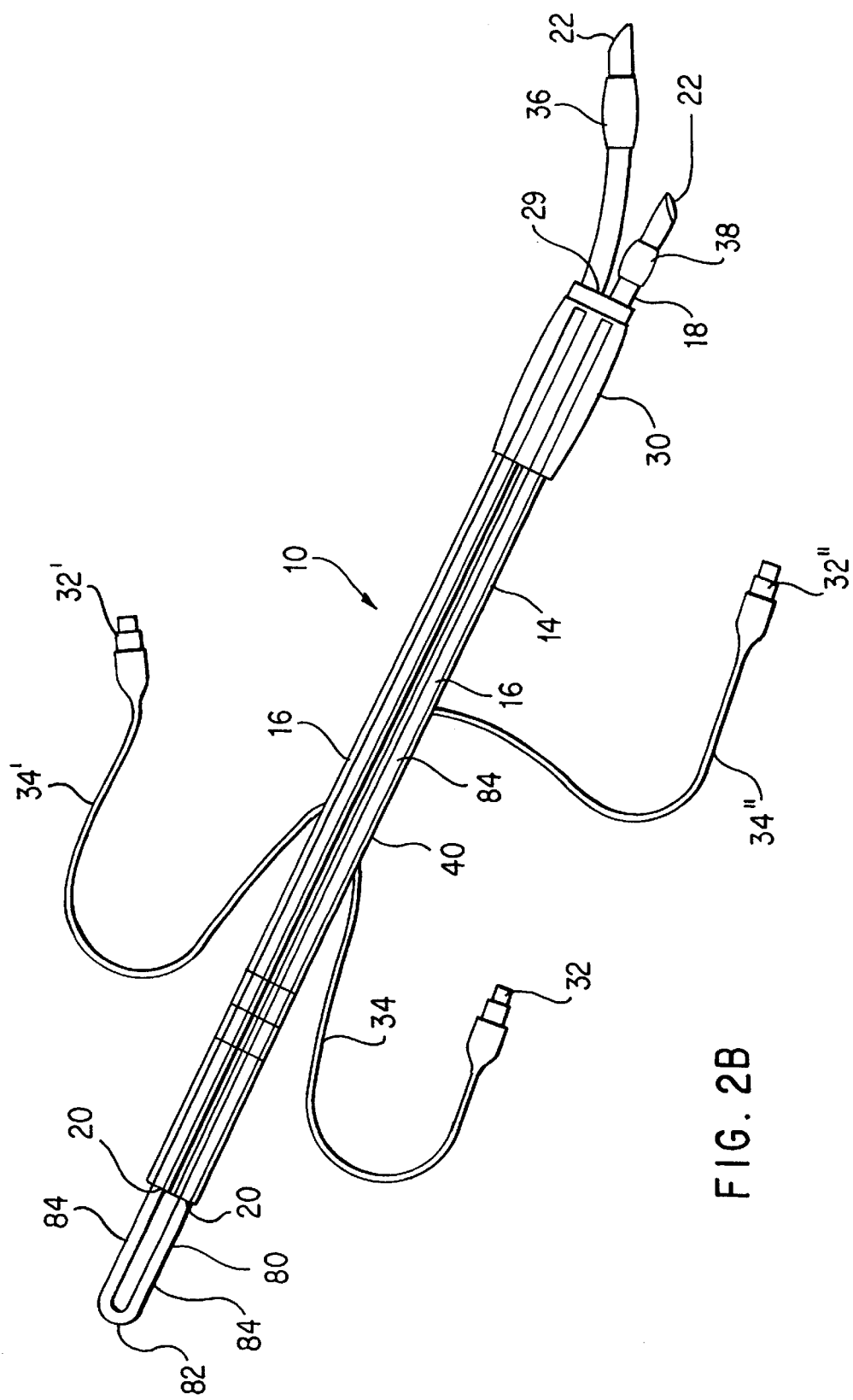
FIG. 2B is a side elevational view of the stylet partially disposed within the lumens of the double lumen tube.
Figure 2C:
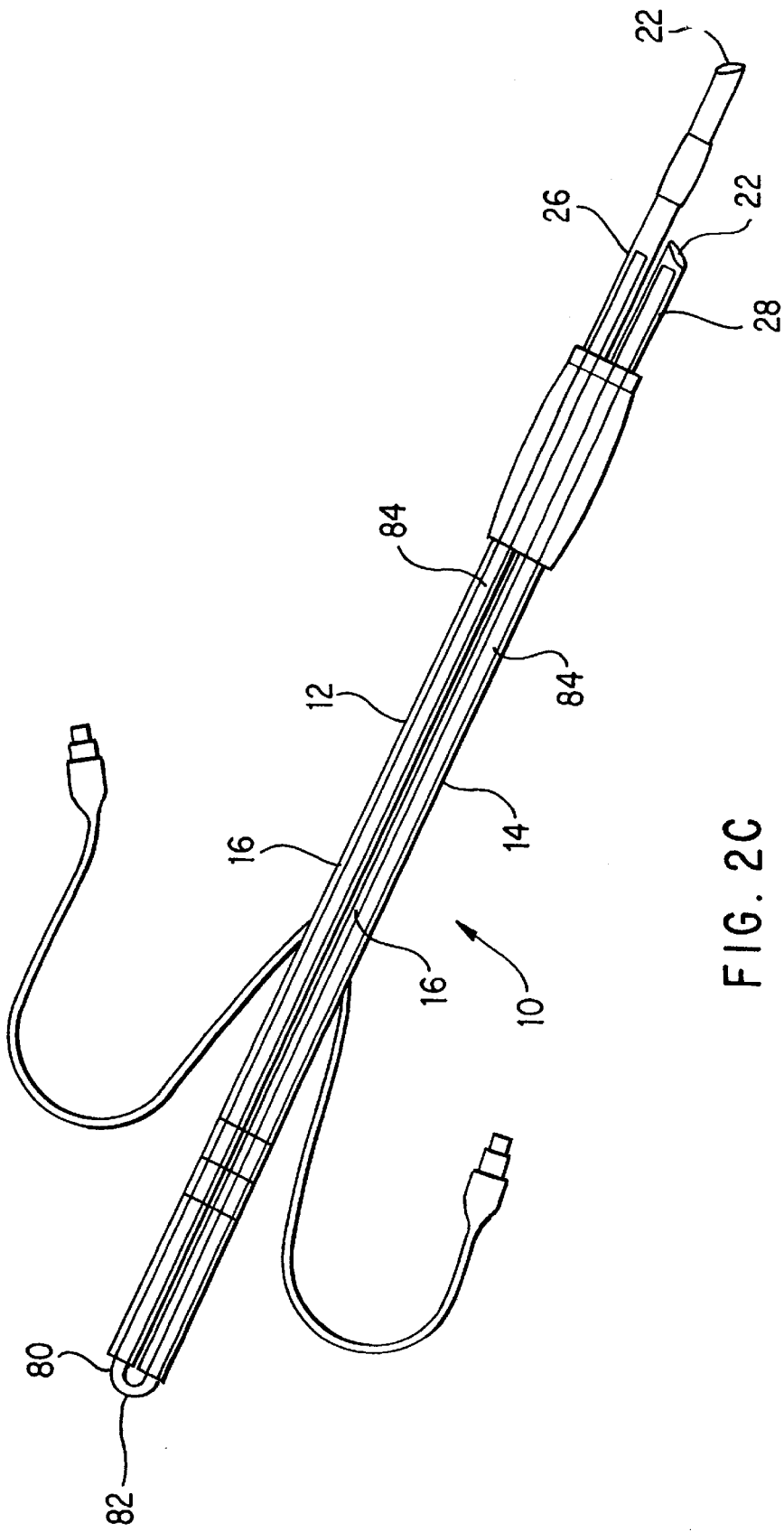
FIG. 2C is a view of FIG. 2B, in which the stylet is fully extended into the lumens, causing the portion of the individual tubes adjacent their distal ends to move together.

Each arm 84 is of a size to fit within the lumen 16 of one tube and extend substantially the length of the tube to be adjacent to its distal end 22. As shown in FIG. 2B, each arm of the stylet 80 is partially inserted into the lumens 16 of the first and second tubes 12, 14. Now referring to FIG. 2C, when each arm 84 of the stylet 80 is moved distally so that the arms 84 extend as far as possible within the lumens 16, at least a portion of the first and second branch sections 26, 28 move from their predisposed spaced-apart positions to contact each other. As will be seen, although the term "contact" is used, the first and second branch sections 26, 28 do not contact each other but are closely adjacent to each other. The stylet 80 can be made of a material that is reusable and able to be sterilized for more than one use. Examples of materials from which the stylet 80 can be formed include, but are not limited to, stainless steel, chromium and alloys, as well as polymers such as polyethylene and other plastics.

Figure 3A:
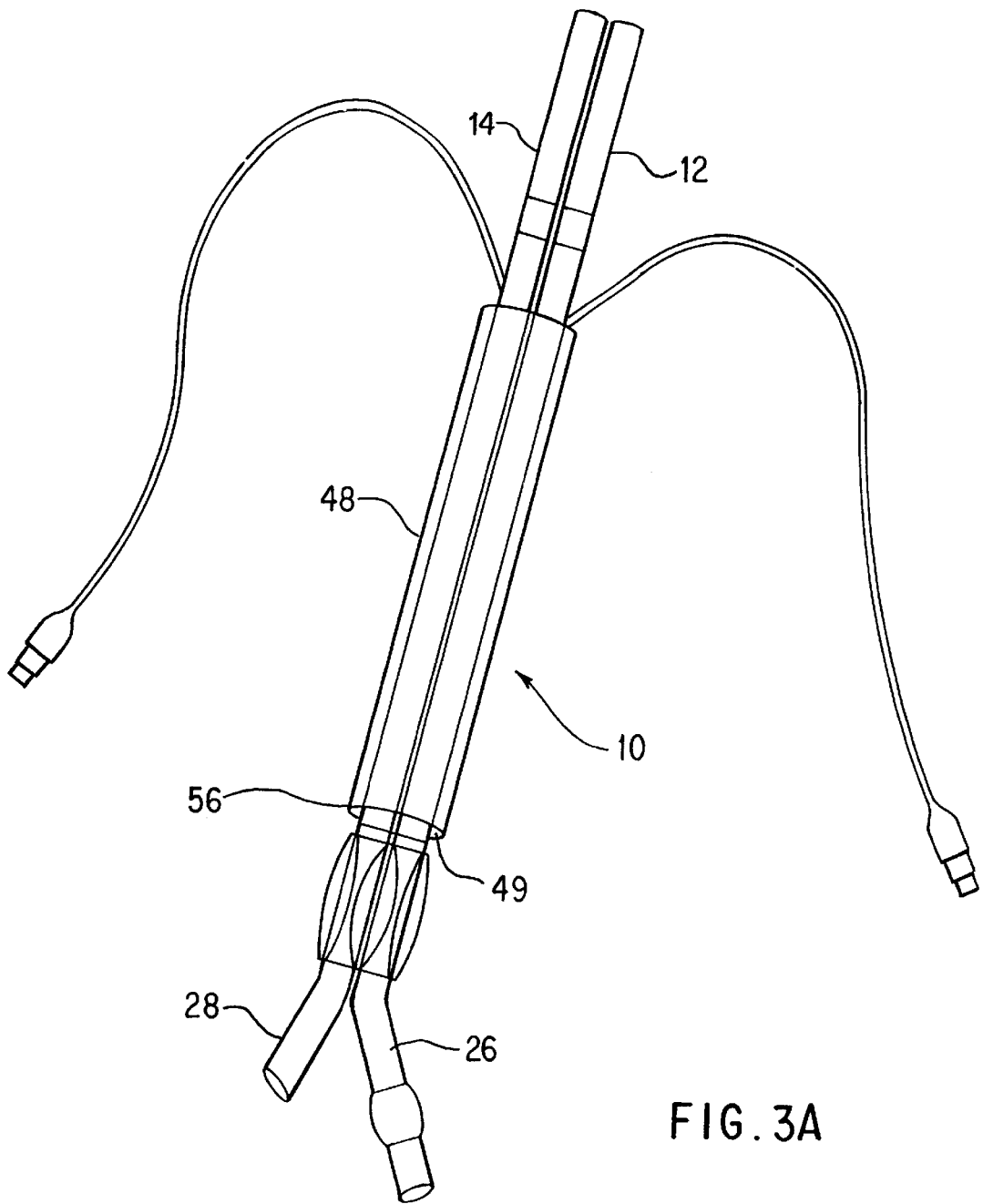
FIG. 3A is a side elevational view of a sleeve partially disposed over the exterior surface of the double lumen tube.
Figure 3B:
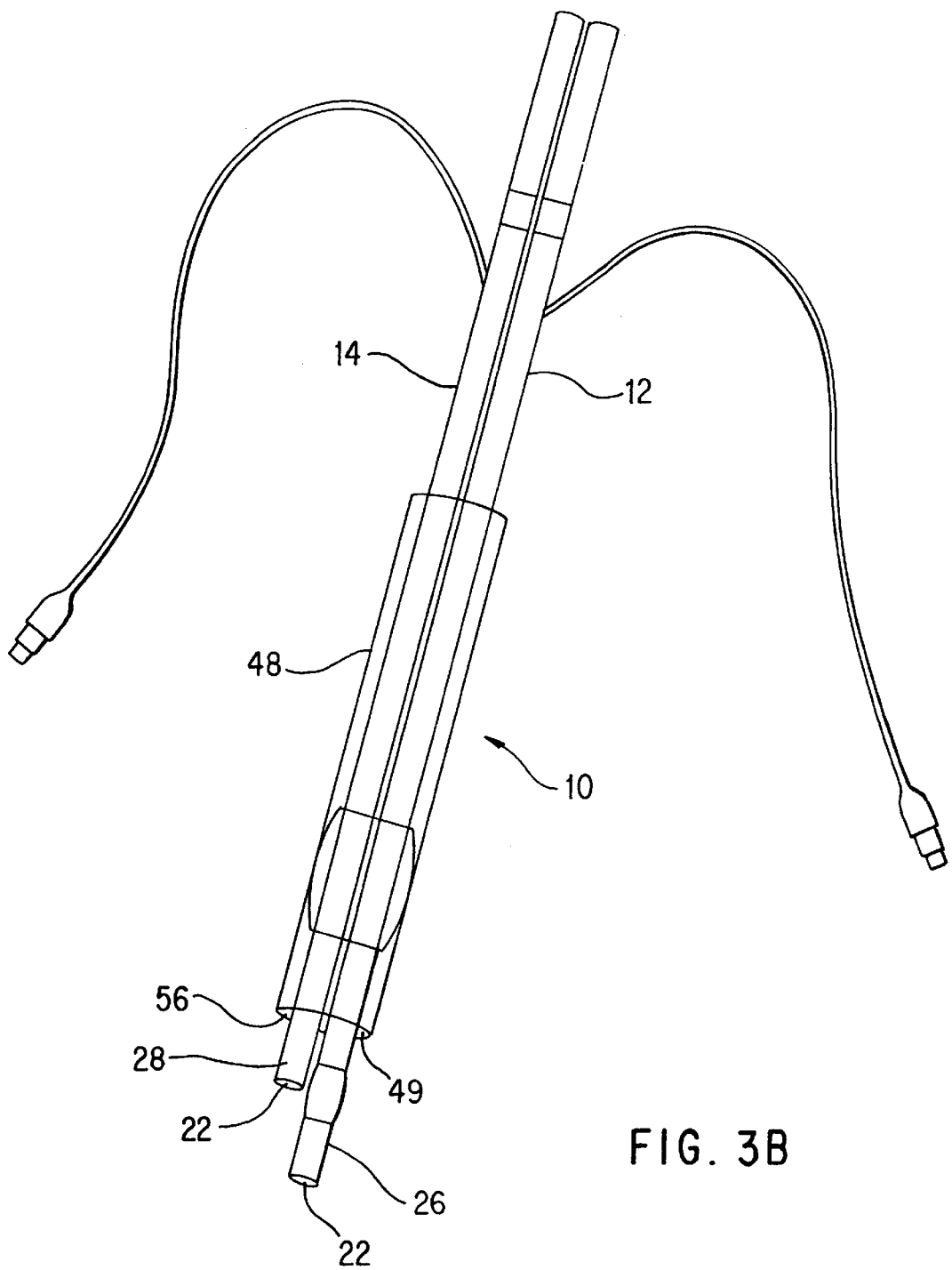
FIG. 3B is a view of FIG. 3A, in which the sleeve is disposed over the exterior surface of the double lumen tube distal to the point at which the two tubes are fixedly attached, causing the portion of the individual tubes adjacent their distal ends to move together.

In another embodiment shown in FIGS. 3A and 3B, the temporary positioning means comprises a sleeve 48. The sleeve 48 has an interior surface 49 of a size to complementarily receive the first tube 12 and the second tube 14 therein. FIG. 3A shows the sleeve 48 extending along a portion of the length of the tubes 12, 14. As shown in FIG. 3B, when the sleeve 48 is moved toward the distal ends 22 of the first tube 12 and the second tube 14 so that the distal ends 22 of each tube 12, 14 are disposed within the sleeve 48 or the sleeve is adjacent to the distal ends 22, at least a portion of the first and second branch sections 26, 28 are in contact with each other. When the clinician moves the sleeve 48 proximally so that the distal end 56 of the sleeve 48 is proximal to or at the lower most or distal most point where the two tubes 12, 14 are fixedly attached, the first branch section 26 and the second branch section 28 move apart to their predisposed spaced-apart position. The sleeve 48 can be made of stainless steel, chromium and alloys, as well as polymers such as polyethylene and other plastics. A plastic sleeve 48 is preferred, however.

Figure 4A:
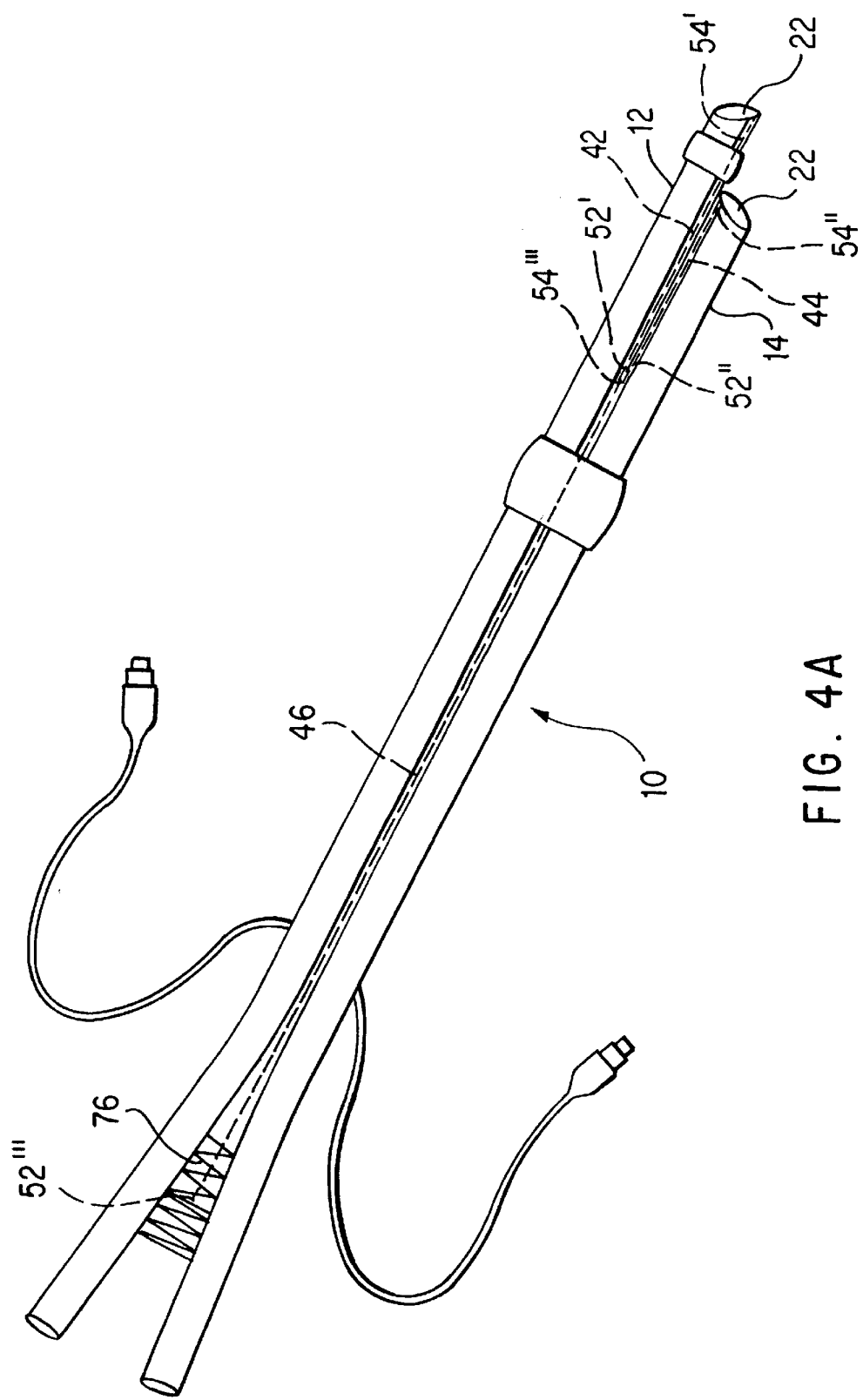
FIG. 4A is a side elevational view of the double lumen tube with wires and a spring structure mechanism, in which the primary spring is in its extended position, causing the first branch section of the first tube and the second branch section of the second tube to be in a contacting or closely adjacent position.

In still another embodiment of the present invention, the temporary positioning means comprises at least one wire and a spring operatively connected to the wires. Referring now to FIG. 4A, this embodiment is shown comprising three wires 42, 44, 46 including a first wire 42, a second wire 44, and a third wire 46, each wire respectively having a top end 52', 52", 52'" and a bottom end 54', 54", 54'". The first and second wires 42, 44 extend along and are disposed adjacent to the first branch section 26 and the second branch section 28, respectively. The bottom end 54' of the first wire 42 is secured adjacent the distal end 22 of the first tube 12 and the bottom end 54" of the second wire 44 is secured adjacent the distal end 22 of the second tube 14. The third wire 46 extends along the joined portion of the length of the first tube 12 and the second tube 14 that are fixedly attached to each other. The bottom end 54'" of the third wire 46 is attached to the top ends 52', 52" of the first and second wires 42, 44 respectively. Each wire 42, 44, 46 extends along the length of its respective tube in a channel which is of a size to complementarily receive the wires 42, 44, 46. Each wire 42, 44, 46 preferably has a diameter of approximately 0.1 millimeters to 0.5 millimeters. In FIG. 4A, the primary spring 76 is in the extended position, and the first branch section 26 and the second branch section 28 are in a contacting or closely adjacent position. Further, referring to FIG. 4B, the primary spring 76 is in the compressed position, and the first branch section 26 and the second branch section 28 are in their predisposed spaced-apart position.

Figure 4B:
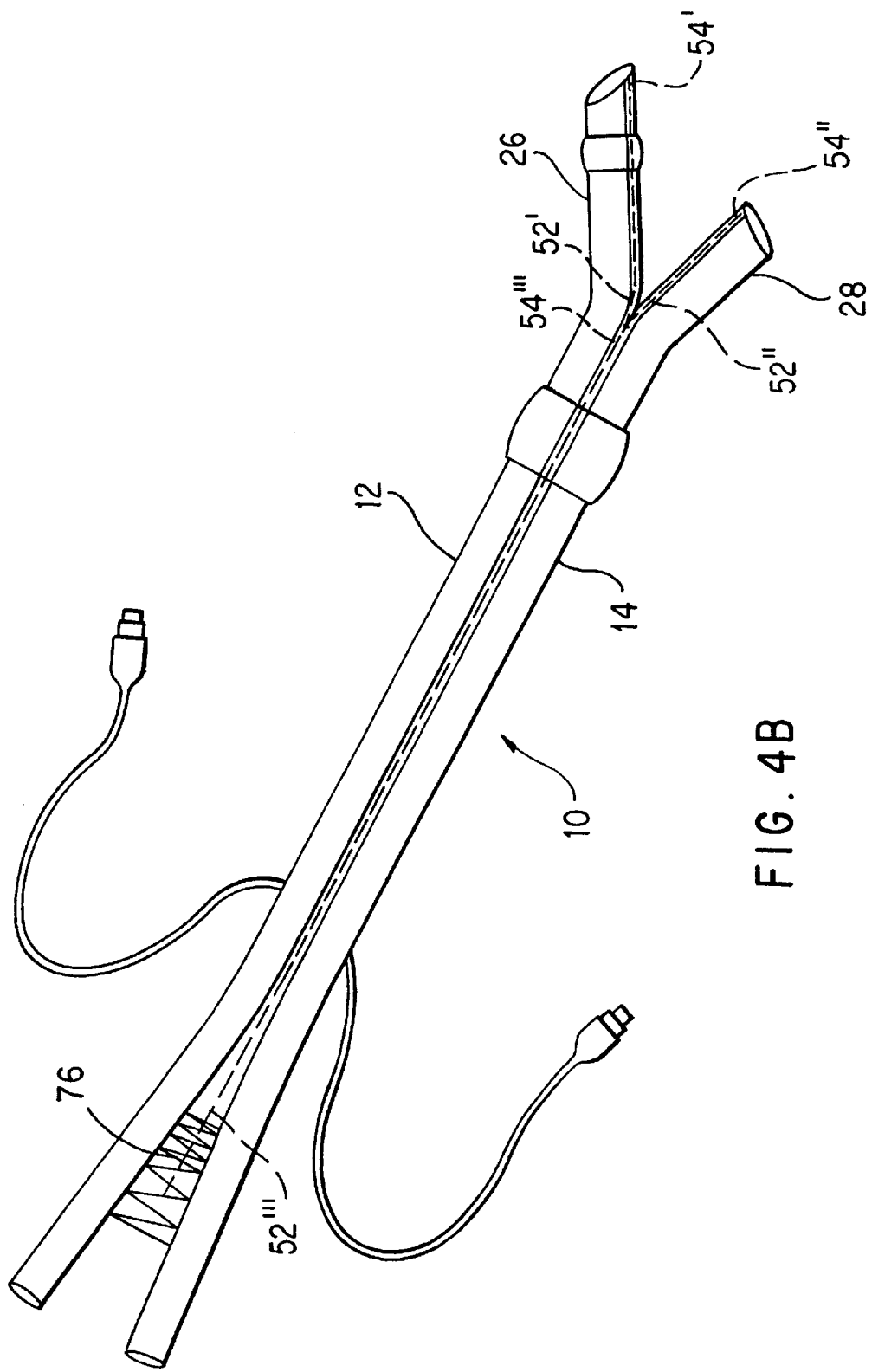
FIG. 4B is a side elevational view of the double lumen tube with wires and a spring structure mechanism, in which the primary spring is in its compressed position, allowing the first branch section of the first tube and the second branch section of the second tube to be in their predisposed spaced-apart position.
Figure 4G:
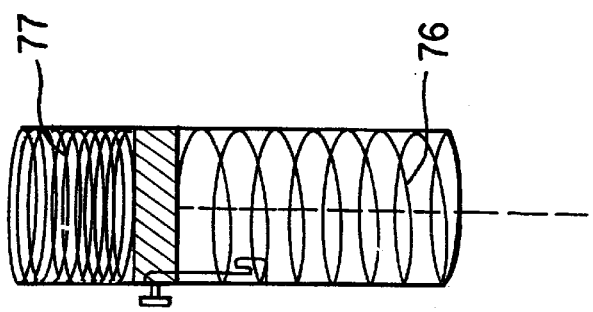
FIG. 4G shows the spring structure of FIG. 4F rotated 90 degrees.
Figure 4F:
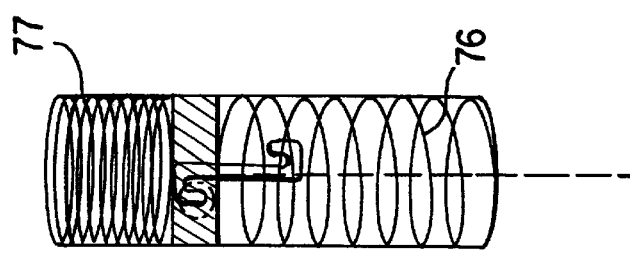
FIG. 4F is a side elevational view of the spring structure with the primary spring in the extended position and the secondary spring opposed to it, in which the double lumen tube is shown schematically.
Figure 4E:
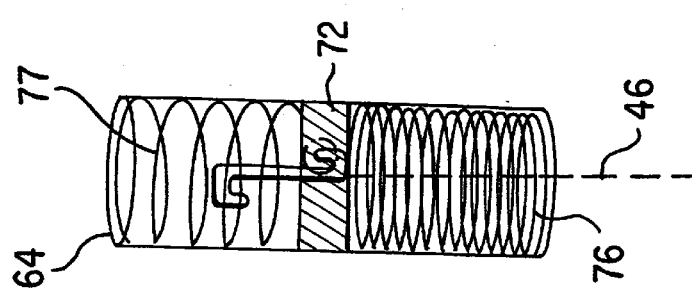
FIG. 4E is a side elevational view of the spring structure with the primary spring in the compressed position and the secondary spring opposed to it, in which the double lumen tube is shown schematically.
Figure 4D:
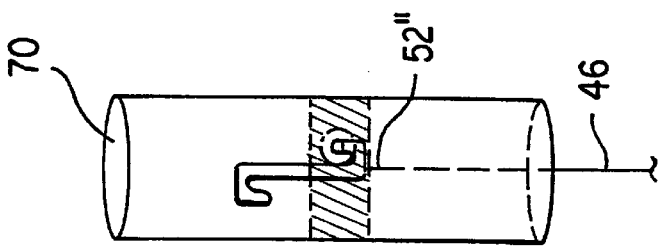
FIG. 4D is a side view of FIG. 4C, showing the plate and protrusion inside the housing.
Figure 4C:
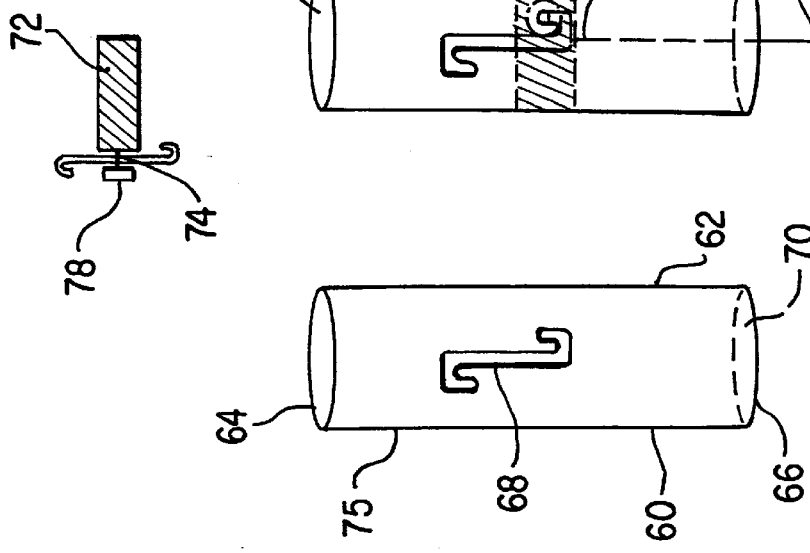
FIG. 4C is a side view of the housing of the spring structure and slot.

Further, referring to FIG. 4C, the device preferably includes a spring structure 75 comprising a housing 60 having an outer surface 62, an upper end 64, and a lower end 66 and defining a bore 70 extending substantially between the upper and lower ends 64, 66. The housing 60 defines a slot 68 interconnecting the bore 70 and the outer surface 62 that extends between a portion of the upper and lower ends 64, 66. Referring to FIGS. 4D and 4D1, a plate 72 is disposed within the bore 70 and slidably movable within the bore 70. The top end 52''' of the third wire 46 is connected to a portion of the plate 72, as shown schematically in FIGS. 4E–4G. The plate 72 also includes a protrusion 74 having an end 78 extending from the plate 72 so that the end 78 of the protrusion 74 extends through the slot 68 of the housing 60. Referring to FIG. 4D1, the protrusion 74 can be a bolt or any other similar device for manually depressing the plate 72 within the bore 70.

Figure 4H:
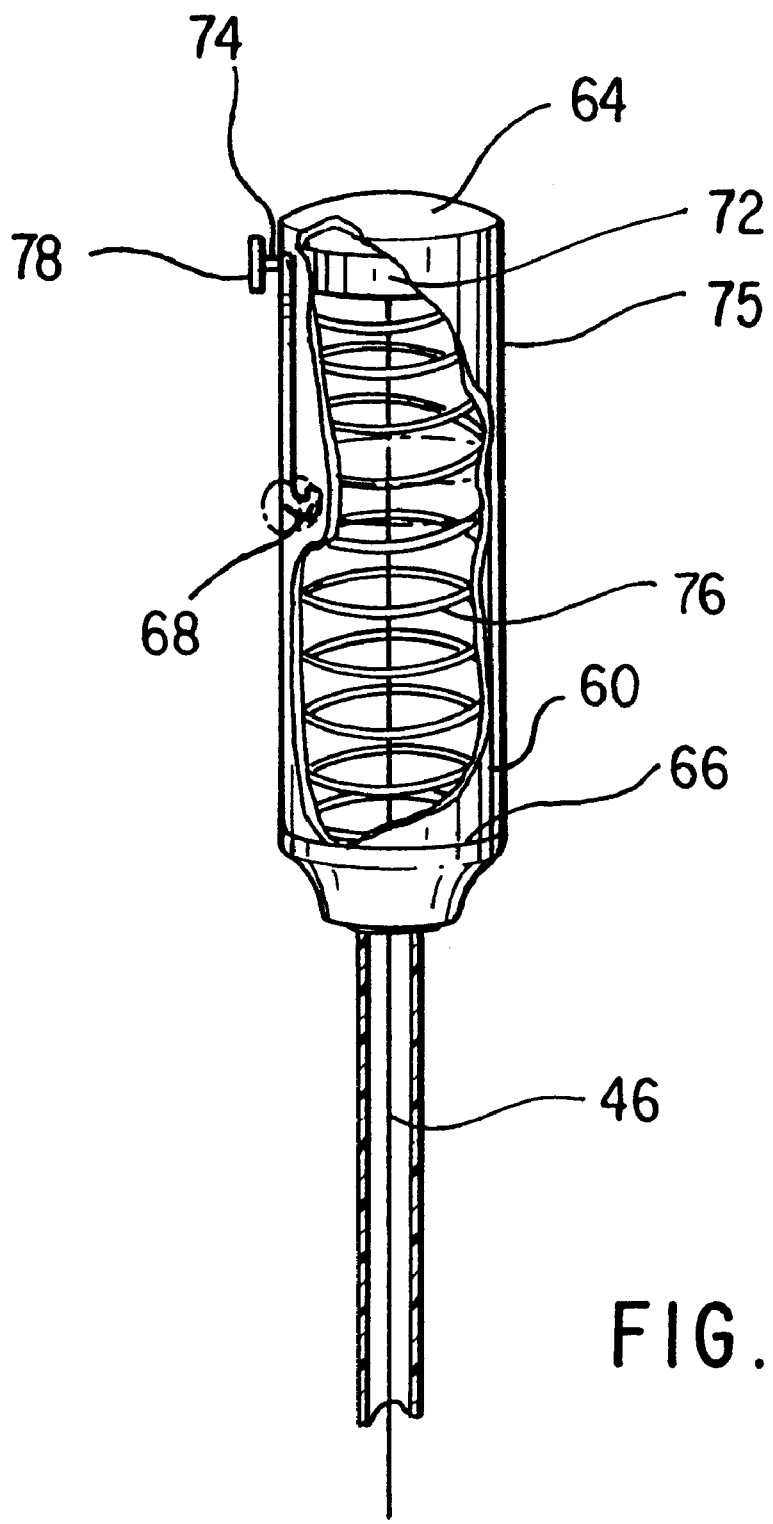
FIG. 4H is a side elevation of the spring structure and the primary spring in the extended position.
Figure 4I:
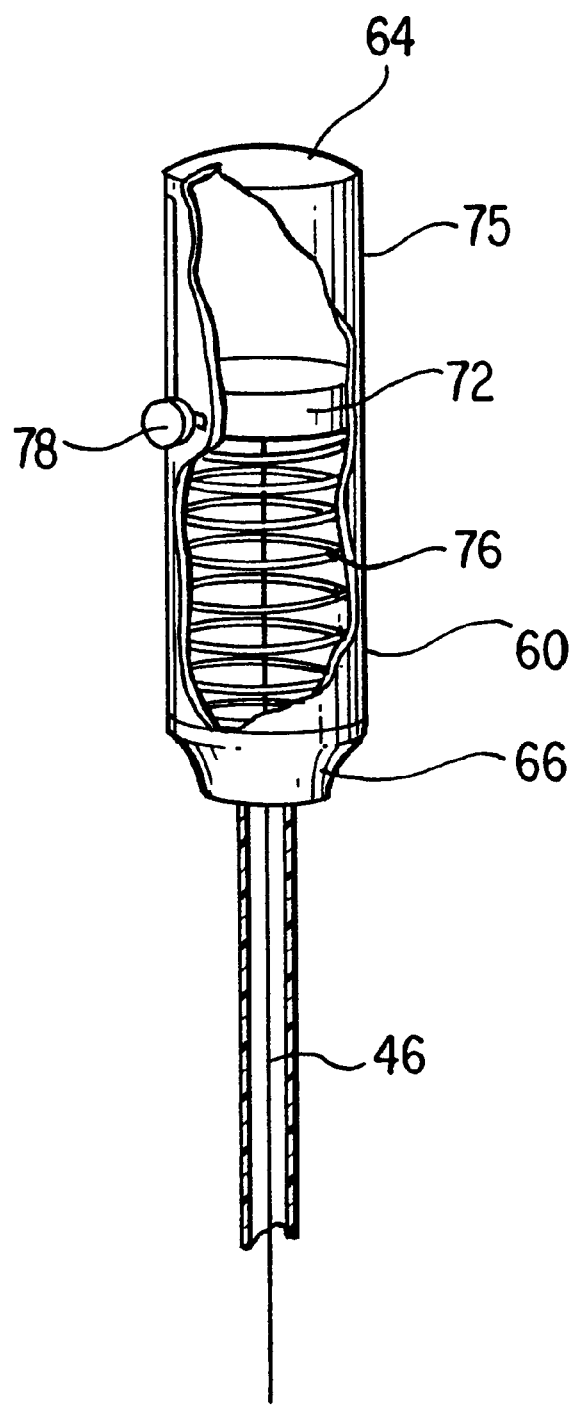
FIG. 4I is a side elevation of the spring structure and the primary spring in the compressed position.

As shown in FIG. 4H, a primary spring 76 is disposed within the housing 60 between its lower end 66 and the plate 72. The primary spring 76 is movable between an extended position, in which the plate 72 is disposed adjacent the upper end 64 of the housing 60, and a compressed position, as shown in FIG. 4I, in which the plate 72 is slid toward the lower end 66 of the housing 60 from the extended position. Referring to FIGS. 4A and 4F, when the primary spring 76 is in the extended position, the first branch section 26 of the first tube 12 and the second branch section 28 of the second tube 14 are in a contacting or closely adjacent position with each other. Alternatively, when the primary spring 76 is in the compressed position, the first branch section 26 of the first tube 12 and the second branch section 28 of the second tube 14 are spread apart from each other, as shown in FIGS. 4B and 4E. To keep the primary spring 76 in the compressed position, the clinician rotates the protrusion 74 into a portion of the slot 68 that extends perpendicularly to the length of the two tubes 12, 14, as shown in FIG. 4D. Once the protrusion is in this portion of the slot 68, the primary spring 76 is held in the compressed position.

Referring back to FIG. 4E, an alternative embodiment of the spring structure 75 comprises a secondary spring 77 which is disposed within the bore 70 of the housing intermediate the upper end 64 thereof and the plate 72, the secondary spring 77 being opposed to the primary spring 76. In this embodiment, the secondary spring 77 stabilizes the plate 72 within the bore 70 so that the plate 72 resists being tilted as the clinician depresses the protrusion 74, thereby compressing the primary spring 76. Further, the secondary spring 77 allows the plate 72 to move more smoothly within the bore 70 by dampening the excursion of the plate 72 within the bore 70. FIG. 4F shows the primary spring 76 in the extended position with the protrusion 74 locked into the slot 68 at the upper end 64 of the housing 60. FIG. 4G is the spring structure 75 rotated 90 degrees. The secondary spring 77 is not required in the present invention, however, because the spring structure functions properly with only the primary spring 76.

Although the embodiment shown in FIGS. 4A–4B is described as using three wires for convenience, one skilled in the art will appreciate that other designs can be used. For example, a single wire can be used, in which the strands are separated to form the first and second wires 42, 44. Likewise, two wires can be used, in which one wire forms the first and second wires 42, 44 and the other wire forms the third wire 46, or one wire forms the first and third wires 42, 46 and the other wire forms the second and third wires 44, 46. However, regardless of the embodiment, the contemplated materials to form the wires 42, 44, 46 are polyvinyl chloride, silicone, stainless steel, titanium and other surgical instrument grade metals.

Referring back to FIG. 1, the breathing tube of the present invention 10 also preferably includes a main inflation cuff 30 circumscribing the exterior surface 18 of both the first tube 12 and the second tube 14. The main inflation cuff 30 has an inflation port 32 and an inflation catheter 34 which extends through the wall 40 of the first tube 12 and connects the cuff to the inflation port 32. By selectively injecting fluid into the main inflation cuff 30, a seal can be made to block air and secretions from escaping from the lungs around the tube 10. When fluid is removed from the main inflation cuff 30, the seal is removed, and air and secretions are able to escape from the lungs around the tube 10. As a person of skill in the art will appreciate, the fluid may be any suitable liquid or gas, the preferred fluid being air.

Still referring to FIG. 1, the present invention preferably also includes a first inflation cuff 36 circumscribing the exterior surface 18 of the first tube 12. Like the main inflation cuff 30, the first inflation cuff 36 has an inflation port 32' and an inflation catheter 34' which extends through the wall 40 of the first tube 12 and connects the cuff to the port. As for the main cuff 30, by selectively injecting fluid into or removing fluid from the first inflation cuff 36, a seal blocks and unblocks, respectively, air and secretions from escaping from the left lung around the first tube 12. Again, the fluid may be any suitable liquid or gas, in which the preferred fluid is air.

Referring to FIG. 2B, another embodiment of the present invention includes a second inflation cuff 38 circumscribing the exterior surface 18 of the second tube 14. The second inflation cuff 38 has an inflation port 32" and an inflation catheter 34" which extends through the wall 40 of the second tube 14 and connects the cuff 38 to the inflation port 32". As for the main cuff 30, by selectively injecting fluid into or removing fluid from the second inflation cuff 38, a seal blocks and unblocks air and secretions from escaping from the right lung around the second tube 14. Again, the fluid may be any suitable liquid or gas, in which the preferred fluid is air.

The present invention also provides a method for ventilating at least one lung of a subject, comprising passing into a trachea of a human subject a breathing tube 10 of the present invention. To safely pass the tube 10 through the vocal cords and into the trachea and bronchi, a clinician must temporarily dispose the first branch section 26 and the second branch section 28 into a contacting or closely adjacent relationship. Of the ways of positioning the first and second branch sections 26, 28 adjacent to each other, one method uses a stylet 80 as described above. The stylet 80 is introduced into the tube 10 prior to intubation of the subject. The first branch section 26 and the second branch section 28 are held in contact by the action exerted by each arm 84 of the stylet 80 on the medial wall 40 of the tube in which it is located. In this contacting position, the two tubes 12, 14 are in the safest configuration for the passage of the breathing tube 10 into the airway of a subject, past the vocal cords into the trachea and bronchi. After the breathing tube 10 has been properly positioned, the stylet 80 is removed by the clinician. Once the stylet 80 is out of the breathing tube 10, the first branch section 26 of the first tube 12 and the second branch section 28 of the second tube 14 resume their predisposed position, in which they are spaced-apart from each other, forming an angle of approximately 50 degrees to 85 degrees. The angle thus formed is the same as the angle formed by the divergence of the left and right mainstem bronchi as they branch from the trachea. After the removal of the stylet 80, the clinician can connect either one or both proximal ends 20 of the double lumen tube 10 to a respirator R, depending on whether one-lung or two-lung ventilation is necessary.

In another method of the present invention, a sleeve 48 temporarily disposes the first branch section 26 and the second branch section 28 in a contacting position with each other. When the clinician slides the sleeve 48 distally so that it circumscribes at least a portion of each tube 12, 14 distal to the point 29 where the two tubes 12, 14 are fixedly attached to each other, the first branch section 26 and the second branch section 28 are in a contacting or closely adjacent position with each other. With the sleeve 48 in this position, the double lumen breathing tube 10 can safely be passed into the airway of a human subject, past the vocal cords into the trachea and mainstem bronchi. Once the tube 10 has been properly positioned, the clinician can slide the sleeve 48 proximally so that the distal end 56 of the sleeve 48 is proximal to the point 29 where the first tube 12 and the second tube 14 are fixedly attached. With the sleeve 48 in this position, the first branch section 26 of the first tube 12 and the second branch section 28 of the second tube 14 are free to return to their predisposed, spaced-apart position. The angle formed between the distal ends 22 of the first tube 12 and the second tube 14 is approximately 50 degrees to 85 degrees, the same angle formed between the left and right mainstem bronchi as they bifurcate from the trachea. After the sleeve 48 has been moved proximally and the first branch section 26 of the first tube 12 and the second branch section 28 of the second tube 14 have entered their respective bronchi, the clinician can connect either one or both proximal ends 16 of the double lumen breathing tube 10 to a respirator R, depending on whether one-lung or two-lung ventilation is necessary.

In another method of temporarily disposing the first branch section 26 of the first tube 12 and the second branch section 28 of the second tube 14 in a contacting or closely adjacent position with each other, a spring structure 75 is used. With the primary spring 76 in its extended position, a plate 72 to which a wire 46 is attached is at the upper end 64 of the housing 60, thereby exerting tension on the wire 46 which is attached to the distal ends 22 of the two tubes 12, 14. When the wire 46 is under tension, the distal ends 22 of the first branch section 26 of the first tube 12 and the second branch section 28 of the second tube 14 are temporarily disposed in a contacting position with each other, thereby permitting a clinician to safely pass the tube 10 through the vocal cords into the trachea and bronchi. Once the tube 10 has been properly positioned, a clinician can depress a protrusion 74 extending from the plate 72 and lock the plate 72 in place by rotating the protrusion 74 into a portion of the slot 68 that extends perpendicularly to the length of the two tubes 12, 14. By compressing the primary spring 76 and reducing the tension on the wire 46, the first branch section 26 of the first tube 12 and the second branch section 28 of the second tube 14 are free to return to their predisposed, spaced-apart position. The angle formed between the distal ends 22 of the first tube 12 and the second tube 14 is approximately 50 degrees to 85 degrees, the same angle formed as they bifurcate from the trachea. After the two tubes 12, 14 have entered their respective bronchi, the clinician can connect either one or both proximal ends of the double lumen 16 breathing tube 10 to a respirator R, depending on whether one-lung or two-lung ventilation is necessary.

The present invention also provides a method for ventilating at least one lung of a subject. In the preferred method, a respirator R is connected to the double lumen breathing tube 10 to provide ventilation to one or both lungs of a subject. In particular, the proximal end 20 of either the first tube 12 or the proximal end 20 of the second tube 14 can be attached to a respirator R which moves a mixture of oxygen and other gases, particularly anesthetics, into and out of the airway of a subject. When a clinician needs to ventilate only the left lung, the proximal end 20 of the first tube 12 is connected to the respirator R and only the left lung will receive the mixture of gases. The proximal end 20 of the second tube 14 can be occluded to prevent ventilation of the right lung. To ensure that no gas is introduced into the right lung, the clinician can inflate the first inflation cuff 36 circumscribing the first tube 12 and the main inflation cuff 30 circumscribing the exterior surface 18 of the first tube 12 and the second tube 14. When both the main inflation cuff 30 and the first inflation cuff 36 are inflated and the respirator R is connected to only the proximal end 20 of the first tube 12, the right lung will not be ventilated.

Alternatively, when a clinician needs to ventilate only the right lung, the proximal end 20 of the second tube 14 is connected to the respirator R and only the right lung will receive the mixture of oxygen and other gases from the respirator R. The proximal end 20 of the first tube 12 can be occluded to prevent ventilation of the left lung. To ensure that no gas is introduced into the left lung, the clinician can inflate the second inflation cuff 38 circumscribing the second tube 14 and the main inflation cuff 30 circumscribing the exterior surface 18 of the first tube 12 and the second tube 14. When both the main inflation cuff 30 and the second inflation cuff 38 are inflated and the respirator R is connected only to the proximal end 20 of the second tube 14, the left lung will not be ventilated.

Although the present invention has been described with reference to specific details of certain embodiments thereof, it is not intended that such details should be regarded as limitations upon the scope of the invention except as and to the extent that they are included in the accompanying claims.

What is claimed is:

1. A breathing tube for ventilating at least one lung of a subject, comprising:

a) two tubes including a first tube and a second tube disposed adjacent to each other, each tube having a lumen, an exterior surface, a proximal end, a distal end, and a length extending between the proximal and distal ends thereof, the first and second tubes fixedly attached to each other along a joined portion of their respective lengths, a first branch section of the length of the first tube being longer than a second branch section of the length of the second tube between the respective distal ends thereof and a location at which the two tubes are fixedly attached to each other, the first branch section and the second branch section predisposed to be spaced-apart from each other;

b) means for temporarily positioning the first branch section and the second branch section in contact with each other adjacent the distal ends thereof;

c) a main inflation cuff circumscribing the exterior surface of the first tube and the second tube, the main inflation cuff having an inflation port and an inflation catheter in fluid communication with the main inflation cuff through the inflation catheter, the main inflation cuff being inflatable and deflatable by adding and removing fluid, respectively, to the main inflation cuff through the inflation catheter; and d) a first inflation cuff circumscribing the exterior surface of the first tube, the first inflation cuff having an inflation port and an inflation catheter in fluid communication with the first inflation cuff through the inflation catheter, the first inflation cuff being inflatable and deflatable by adding and removing fluid, respectively, to the first inflation cuff through the inflation catheter.

2. The breathing tube of claim 1, further comprising a second inflation cuff circumscribing the exterior surface of the second tube, the second inflation cuff having an inflation port and an inflation catheter in fluid communication with the second inflation cuff through the inflation catheter, the second inflation cuff being inflatable and deflatable by adding and removing fluid, respectively, to the second inflation cuff through the inflation catheter.

3. The breathing tube of claim 1, wherein the temporarily positioning means comprises a stylet, having a central body portion connecting two spaced-apart arms that are disposed substantially parallel to each other so that the stylet is substantially U-shaped in plan view, each arm being of a size to be disposed within the lumen of one tube and extending substantially the length of the tube to its distal end, the arms of the stylet, when each disposed in one of the two tubes, position at least a portion of the first branch section and the second branch section of the two tubes in contact with each other.

4. The breathing tube of claim 1, wherein the temporarily positioning means comprises a sleeve, having an interior surface of a size to complementarily receive the first and second tubes therein, wherein, when the first and second tubes are disposed within the sleeve, at least a portion of the first branch section and the second branch section of the two tubes is positioned to be in contact with each other.

5. The breathing tube of claim 1, wherein the temporarily positioning means comprises:
   a) three wires including a first wire, a second wire, and a third wire, each wire having a top end and a bottom end, the first and second wires extending along and disposed adjacent to the first branch section and the second branch section respectively, wherein the bottom end of the first wire is secured to the distal end of the first tube and the bottom end of the second wire is secured to the distal end of the second tube, wherein the third wire extends along the joined portion of the length of the first and second tubes that are fixedly attached to each other, wherein the bottom end of the third wire is attached to the top ends of the first and second wires;
   b) a spring structure comprising:
      i) a housing having an outer surface, an upper end, and a lower end and defining a bore extending between the upper and lower ends, the housing having a slot interconnecting the bore and the outer surface that extends intermediate the upper and lower ends;
      ii) a plate disposed within the bore and slidably movable within the bore, wherein the top end of the third wire is connected to a portion of the plate, the plate including a protrusion having an end extending from a portion of the plate so that the end of the protrusion extends through the slot of the housing; and
      iii) a primary spring disposed within the bore of the housing intermediate the lower end thereof and the plate, the primary spring is movable between an extended position, in which the plate is disposed adjacent the upper end of the housing so that the first and second tubes are in contact with each other adjacent the distal ends thereof, and a compressed position, in which the plate is slid toward the lower end of the housing from the extended position so that the first branch section of the first tube and the second branch section of the second tube are spread apart from each other.

6. The breathing tube of claim 5, further comprising a secondary spring disposed within the bore of the housing intermediate the upper end thereof and the plate, the secondary spring being opposed to the primary spring.

7. The breathing tube of claim 1, wherein the length of the first branch section of the first tube between the distal end thereof and the location at which the two tubes are fixedly attached to each other is 1.5 centimeters to 3.5 centimeters longer than the length of the second branch section of the second tube between the distal end thereof and the location at which the two tubes are fixedly attached to each other.

8. The breathing tube of claim 1, wherein when the second tube is oriented substantially linearly along its length, the first branch section of the first tube between the distal end thereof and the location at which the two tubes are fixedly attached to each other is predisposed to form an angle of approximately 35 degrees to 50 degrees relative to the substantially linearly oriented second tube.

9. The breathing tube of claim 1, wherein when the first tube is oriented substantially linearly along its length, the second branch section of the second tube between the distal end thereof and the location at which the two tubes are fixedly attached to each other is predisposed to form an angle of approximately 15 degrees to 35 degrees relative to the substantially linearly oriented first tube.

10. A breathing tube for ventilating at least one lung of a subject, comprising:
   a) a respirator;
   b) two tubes including a first tube and a second tube disposed adjacent to each other, each tube having a lumen, an exterior surface, a proximal end, a distal end, and a length extending between the proximal and distal ends thereof, the first and second tubes fixedly attached to each other along a joined portion of their respective lengths, a first branch section of the length of the first tube being longer than a second branch section of the length of the second tube between the respective distal ends thereof and a location at which the two tubes are fixedly attached to each other, the first branch section and the second branch section predisposed to be spaced-apart from each other, the proximal end of at least one tube being detachably connected to the respirator;
   c) means for temporarily positioning the first tube and the second tube in contact with each other adjacent the distal ends thereof;
   d) a main inflation cuff circumscribing the exterior surface of the first tube and the second tube, the main inflation cuff having an inflation port and an inflation catheter in fluid communication with the main inflation cuff through the inflation catheter, the main inflation cuff being inflatable and deflatable by adding and removing fluid, respectively, to the inflation cuff through the inflation catheter; and
   e) a first inflation cuff circumscribing the exterior surface of the first tube, the first inflation cuff connected to a first inflation port by a first inflation catheter.

11. A breathing tube for ventilating at least one lung of a subject, comprising:
   a) two tubes including a first tube and a second tube disposed adjacent to each other, each tube having a lumen, an exterior surface, a proximal end, a distal end, and a length extending between the proximal and distal ends thereof, the first and second tubes fixedly attached to each other along a joined portion of their respective lengths, a first branch section of the length of the first tube being longer than a second branch section of the length of the second tube between the respective distal ends thereof and a location at which the two tubes are fixedly attached to each other, the first branch section and the second branch section predisposed to be spaced-apart from each other;

b) three wires including a first wire, a second wire, and a third wire, each wire having a top end and a bottom end, the first and second wires extending along and disposed adjacent to the first branch section and the second branch section respectively, wherein the bottom end of the first wire is secured to the distal end of the first tube and the bottom end of the second wire is secured to the distal end of the second tube, wherein the third wire extends along the joined portion of the length of the first and second tubes that are fixedly attached to each other, wherein the bottom end of the third wire is attached to the top ends of the first and second wires;

c) a spring structure comprising:
  i) a housing having an outer surface, an upper end, and a lower end and defining a bore extending between the upper and lower ends, the housing having a slot interconnecting the bore and the outer surface that extends intermediate the upper and lower ends;
  ii) a plate disposed within the bore and slidably movable within the bore, wherein the top end of the third wire is connected to a portion of the plate, the plate including a protrusion having an end extending from a portion of the plate so that the end of the protrusion extends through the slot of the housing; and
  iii) a primary spring disposed within the bore of the housing intermediate the lower end thereof and the plate, the primary spring is movable between an extended position, in which the plate is disposed adjacent the upper end of the housing so that the first and second tubes are in contact with each other adjacent the distal ends thereof, and a compressed position, in which the plate is slid toward the lower end of the housing from the extended position so that the first branch of the first tube and the second branch of the second tube are spread apart from each other;

d) a main inflation cuff circumscribing the exterior surface of the first tube and the second tube, the main inflation cuff having an inflation port and an inflation catheter in fluid communication with the main inflation cuff through the inflation catheter, the main inflation cuff being inflatable and deflatable by adding and removing fluid, respectively, to the main inflation cuff through the inflation catheter; and e) a first inflation cuff circumscribing the exterior surface of the first tube, the first inflation cuff having an inflation port and an inflation catheter in fluid communication with the first inflation cuff through the inflation catheter, the first inflation cuff being inflatable and deflatable by adding and removing fluid, respectively, to the first inflation cuff through the inflation catheter.

12. The breathing tube of claim 11, further comprising a secondary spring disposed within the bore of the housing intermediate the upper end thereof and the plate, the secondary spring being opposed to the primary spring.

13. The breathing tube of claim 11, wherein the length of the first branch section of the first tube between the distal end thereof and the location at which the two tubes are fixedly attached to each other is 1.5 centimeters to 3.5 centimeters longer than the length of the second branch section of the second tube between the distal end thereof and the location at which the two tubes are fixedly attached to each other.

14. The breathing tube of claim 11, wherein when the second tube is oriented substantially linearly along its length, the first branch section of the first tube between the distal end thereof and the location at which the two tubes are fixedly attached to each other is predisposed to form an angle of approximately 35 degrees to 50 degrees relative to the substantially linearly oriented second tube.

15. The breathing tube of claim 11, wherein when the first tube is oriented substantially linearly along its length, the second branch section of the second tube between the distal end thereof and the location at which the two tubes are fixedly attached to each other is predisposed to form an angle of approximately 15 degrees to 35 degrees relative to the substantially linearly oriented first tube.

16. A method of ventilating at least one lung of a subject, comprising the steps of:
  a) passing into a trachea of the subject a breathing tube comprising two tubes including a first tube and a second tube disposed adjacent to each other, each tube having a lumen, an exterior surface, a proximal end, a distal end, and a length extending between the proximal and distal ends thereof, the first and second tubes fixedly attached to each other along a joined portion of their respective lengths, a first branch section of the length of the first tube being longer than a second branch section of the length of the second tube between the respective distal ends thereof and a location at which the two tubes are fixedly attached to each other, the first branch section and the second branch section predisposed to be spaced-apart from each other, the proximal end of at least one tube being adapted to detachably connect to a respirator;
  b) temporarily disposing the first branch section of the first tube and the second branch section of the second tube in a contacting relationship;
  c) inserting the breathing tube into and through a larynx of the subject;
  d) after the inserting step, allowing the sections of the two tubes adjacent the distal ends thereof to move to their predisposed spaced-apart positions;
  e) further advancing the breathing tube so that the distal end of the first tube enters a left mainstem bronchus of the subject;
  f) inflating an inflation cuff circumscribing at least the first tube; and
  g) connecting at least one proximal end of the first tube and the second tube to the respirator.

17. The method of claim 16, wherein the inflation cuff is a main inflation cuff circumscribing the exterior surface of the first tube and the second tube, the main inflation cuff having an inflation port and an inflation catheter in fluid communication with the main inflation cuff through the inflation catheter, the main inflation cuff being inflatable and deflatable by adding and removing fluid, respectively, to the main inflation cuff through the inflation catheter.

18. The method of claim 16, wherein the inflation cuff is a first inflation cuff circumscribing the exterior surface of the first tube, the first inflation cuff having an inflation port and an inflation catheter in fluid communication with the first inflation cuff through the inflation catheter, the first inflation cuff being inflatable and deflatable by adding and removing fluid, respectively, to the first inflation cuff through the inflation catheter.

* * * * *